United States Patent

Powers et al.

[11] Patent Number: 5,633,468
[45] Date of Patent: May 27, 1997

[54] MONITORING OF FUEL PARTICLE COATING CRACKING

[75] Inventors: Thomas Powers, Lynchburg; Donald M. Stevens, Lovingston; John E. Coulter, Lynchburg, all of Va.

[73] Assignee: The Babcock & Wilcox Company, New Orleans, La.

[21] Appl. No.: 527,603

[22] Filed: Sep. 13, 1995

[51] Int. Cl.$^6$ ................................................. G01N 29/04
[52] U.S. Cl. ........................................... 73/801; 73/587
[58] Field of Search ............................ 73/801, 587, 645

[56] References Cited

U.S. PATENT DOCUMENTS

| | | | |
|---|---|---|---|
| 4,591,478 | 5/1986 | Cohen et al. | 376/253 |
| 5,005,415 | 4/1991 | Holroyd | 73/801 |
| 5,156,802 | 10/1992 | Robertson et al. | 376/245 |
| 5,459,767 | 10/1995 | Lessing | 73/821 |
| 5,502,561 | 3/1996 | Hutchins et al. | 356/336 |

*Primary Examiner*—Richard Chilcot
*Assistant Examiner*—Max H. Noori
*Attorney, Agent, or Firm*—Daniel S. Kalka; Robert J. Edwards

[57] ABSTRACT

An apparatus and method are disclosed for determining the integrity of coated nuclear fuel particles by evaluating acoustic parameter measurements of the particles during controlled loading.

5 Claims, 3 Drawing Sheets

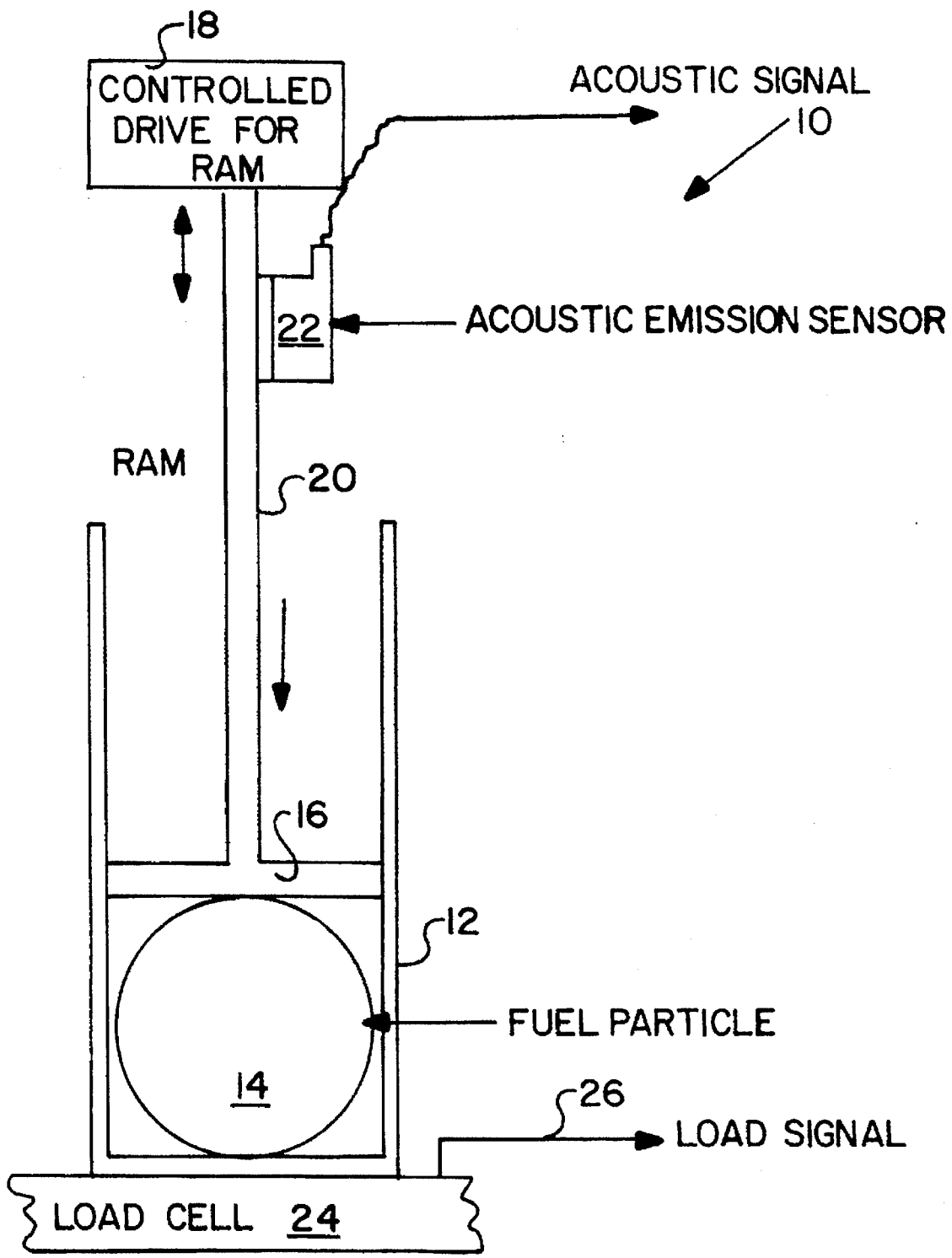

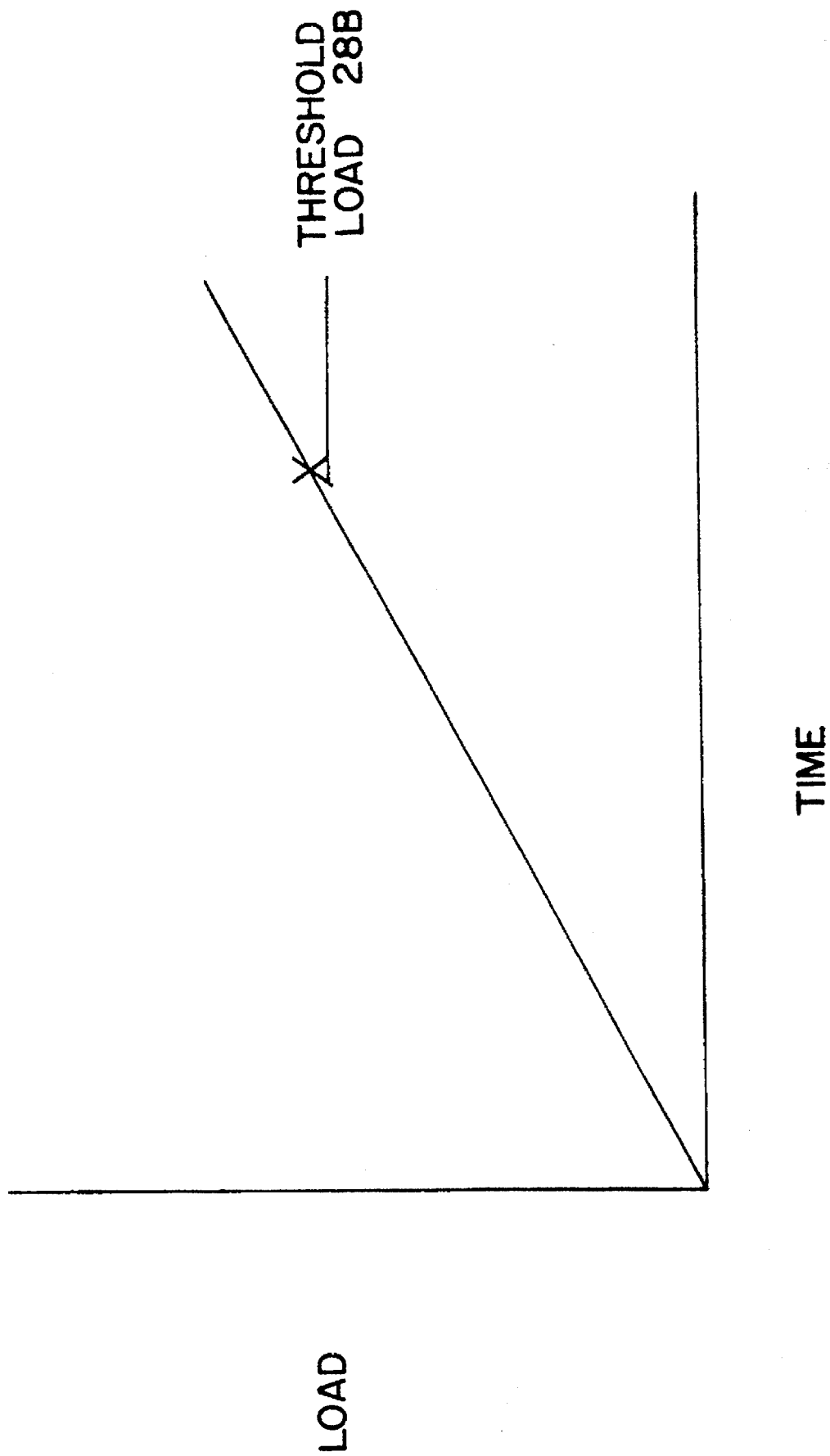

MONITORING OF FUEL PARTICLE COATING CRACKING

BACKGROUND OF THE INVENTION

1. Field of the Invention

The present invention relates in general to techniques for determining particle coating integrity, and in particular, to a characterization technique for determining the integrity of outer coatings on nuclear fuel particles.

2. Description of the Related Art

In a new design particle bed reactor (PBR), a typical fuel rod consists of millions of tiny multi-layered spherical fuel particles, each having a nominal diameter of roughly about 500 microns (μm). The innermost "kernel" of each particle consists of enriched uranium. The intermediate layers of each particle consist of buffering carbon layers. The outermost layer of each particle consists of a thin coating of a metallic carbide whose primary purpose is to serve as a barrier against escaping fission products. It is readily understood that maintaining the integrity of the fuel particle's outer carbide layer is of the utmost importance.

Currently, there are few inspection techniques applicable to determining the integrity of such particles. Most of these techniques are destructive in nature. Apparatus and methods are also known for acoustic characterization of the integrity of the outer coating on nuclear fuel particles and for differentiating between flawed and unflawed specimen. In these known techniques, the particles to be tested are individually dropped on a piezoelectric acoustic transducer to generate an electrical signal indicative of the integrity of the coating on the dropped particle. Signal analysis is then utilized to evaluate the data showing the acoustic differences between a flawed and unflawed particle by comparing each signal response with that of a calibrated standard of an unflawed particle.

For the apparatus described above, the signal analysis means comprises an amplifier and an analog-to-digital (A/D) converter to amplify the signal and input it into a computer which houses digital analysis software. Differences in the signal response enable discrimination between flawed and unflawed particles. The above method and apparatus is more fully disclosed in U.S. Pat. No. 5,156,802 assigned to the Babcock and Wilcox Company.

From the foregoing it is seen that there exists a need for nondestructive inspection techniques for predicting, prior to particle failure, the integrity of the above discussed nuclear fuel particles which can offer reproducible and reliable results. Prior art techniques rely upon discriminating between failed and unfailed specimen. The present invention offers an avenue to predict whether a given particle or batches of particles will fail if subjected to a given load, without actually subjecting the particles to the destructive load.

SUMMARY OF THE INVENTION

The present invention is directed to solving the problems associated with prior art techniques as well as others by providing an apparatus and an improved method for predicting the integrity of nuclear fuel particles by detecting, very early, the onset of outer coating crack initiation during a controlled loading procedure of a selected statistical sample of particles. In this invention, individual fuel particles from a given sample are subjected to a controlled load derived from a ram type device. The ram has an acoustic monitoring device mounted thereon and being in intimate contact with the individual fuel particle being tested is thus able to monitor the acoustic output of the fuel particle during load application with highly sensitive acoustic emission sensors. Stress waves generated from the rapid release of energy during the load-derived particle crack initiation are propagated through the ram where they are subsequently detected by the acoustic emission sensors. By detecting the onset of cracking as a function of a threshold load, predictions can be made as to the integrity of the sample tested and of sample batches of particles by comparisons between particles of known integrities to those of unknown integrities.

Accordingly, an object of the present invention is to provide an acoustic technique for predicting nuclear fuel particle coating integrity as a function of applied load.

Another object of the present invention is to provide a technique for fuel particle coating evaluation that is more sensitive to crack initiation thus allowing better sample evaluation and coating failure characterization.

These and other objects along with the various features of novelty which characterize the invention are pointed out with particularity in the claims annexed to and forming part of this disclosure. For a better understanding of the present invention, and the operating advantages attained by its use, reference is made to the accompanying drawings and descriptive matter in which the preferred embodiment of the invention is illustrated.

BRIEF DESCRIPTION OF THE DRAWINGS

In the drawings:

FIG. 1 is a schematic view of the fuel particle system in accordance with the present invention.

DETAILED DESCRIPTION OF THE PREFERRED EMBODIMENT

Figure 2:
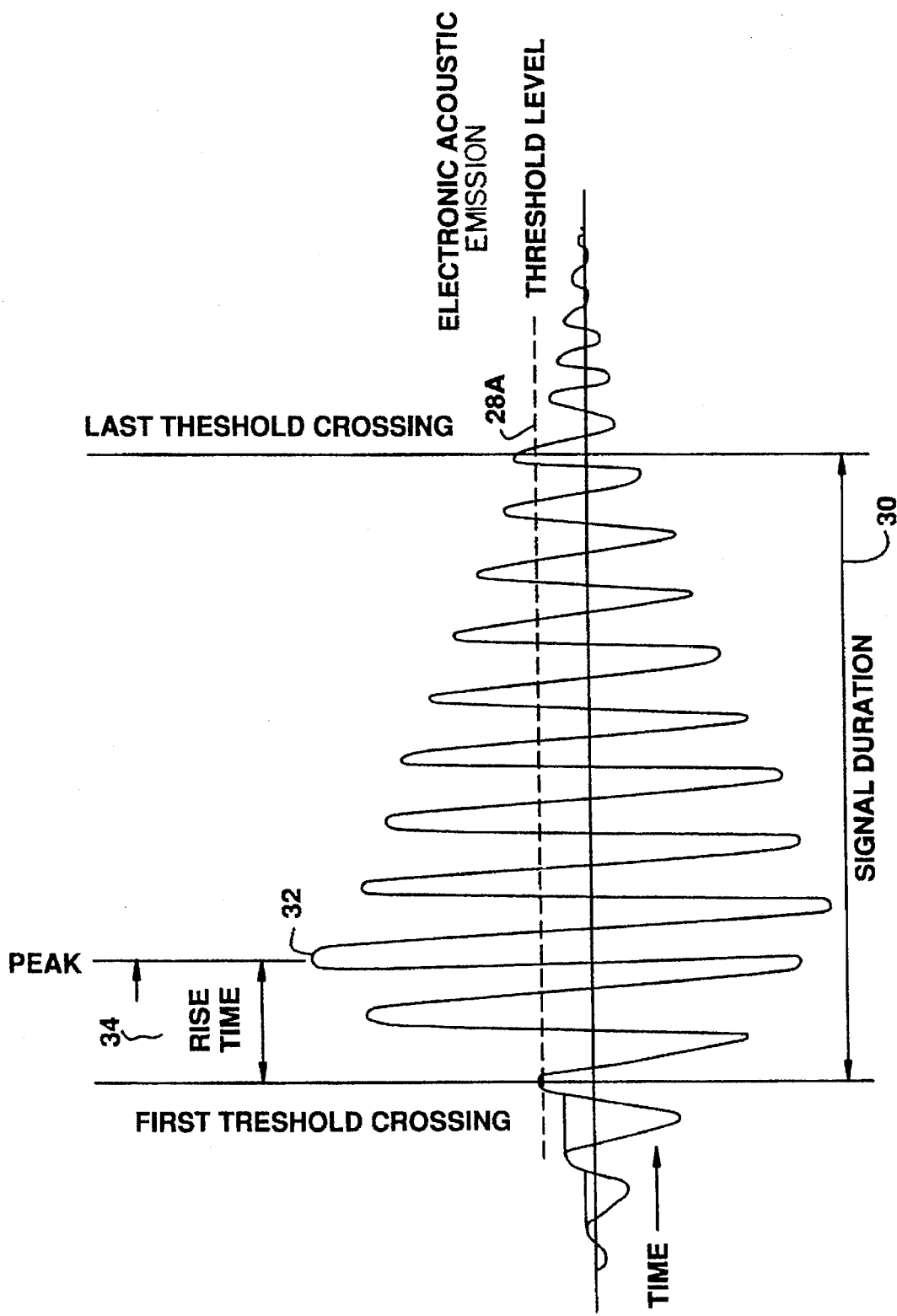
FIG. 2 is an illustration of the acoustic emission signal attributes generated in the FIG. 1 system.

Referring now to the drawings it will be understood that the embodiments therein are intended to depict a preferred embodiment of the present invention and not to limit it thereto.

Fuel for a specialized particle bed reactor (PBR), takes the form of millions of tiny multi-layered spherical nuclear fuel particles on the order of 0.730 mm in average diameter. The innermost kernel of these particles contains the enriched uranium. Intermediate layers of carbon are then sandwiched between the kernel and a layer of silicon carbide (SiC). The SiC layer of the particle serves as a containment for the fission products in the kernel and maintaining the integrity of this coating is thus of critical importance.

In the acoustic emission technique of the present invention, as applied to the inspection of fuel particles, acoustic emissions are derived from the onset of cracking of an individual fuel particle as sensed by a highly sensitive transducer located on the ram applying a controlled load to the particle.

Through correlations between acoustic emission activity and applied stresses resulting from the loading associated with the ram, insight is offered into the overall expected integrity of the particle's outer coating, thus allowing for the capability of predicting integrity of a given batch of particles from a statistical sampling.

The apparatus associated with the preferred embodiment is described in FIG. 1. The particle testing apparatus 10 includes a container 12 into which an individual fuel particle 14 is located. The particle 14 is then subjected to a compression force from a ram 16 which is controllably driven down onto the fuel particle 14 by a controlled motor drive 18 connected to the ram 16 by a shaft 20. The ram 16, being in intimate contact with the individual fuel particle, is thus monitored with highly sensitive acoustic emission sensor 22 mounted to the shaft 20. Stress waves generated from the rapid release of energy during load-derived particle crack initiation are propagated through the ram 16 where they are transmitted to the shaft 20 and subsequently are detected by the acoustic emission sensor 22. Since the container 12 is mounted on a load cell 24, the load placed on the fuel particle 14 is constantly monitored by the load cell 24 which outputs a signal indicative of the load along line 26. The load cell output signal as a function of time can be plotted as in FIG. 1A. By detecting the onset of cracking as a function of load, predictions can be made as to the integrity of sample batches of particles as well as comparisons enabled between particles of known integrities to those of unknown integrities by a comparison of the characteristics of the load vs. acoustic signal outputs between the two classes. This comparison of the acoustic signal outputs will yield a load threshold, 28B, which corresponds to the load at which incipient cracking of the fuel particle coating occurs.

With particular reference to FIG. 2, it is seen that a typical acoustic signal from the acoustic sensor 22 is monitored to determine the integrity of the particle without destroying same.

As previously mentioned, a load threshold level 28B is determined after which fuel particle cracking can be expected to occur. The ram 16 is then driven down onto the fuel particle 14 while the output of the sensor is monitored. An electronic acoustic emission threshold 28A representing a level above the always present electronic noise is set. Any stress load giving rise to an acoustic event above the electronic threshold is detected. The controlled drive is then disabled and the acoustic signal is allowed to dampen down to a level below the electronic threshold level 28A. The signal duration 30 between the first threshold crossing and the last threshold crossing is then measured in a known manner along with the peak amplitude 32 of the periodic waveform during the signal duration 30 as well as the rise time 34 from the first threshold crossing to the peak amplitude 32. These measured parameters can then be analyzed, correlated with load, and utilized as a predictor of the integrity of sample batches of particles as well as to compare responses between particles of known integrities to those of unknown integrities.

A sufficient statistical number of fuel particles 14 is tested in the above described manner to thereby identify the integrity of the fuel particle bed without destroying any of the fuel particles 14.

During application of the load, the particles may be positioned in a furnace under a helium cover gas. A graphite ram may be employed attached to a linear variable differential transformer (LVDT). Typical measured particle failure loads at 1000° C. was a failure load of 1900 g (grams load) and at 1500° C., a failure load of 3500 g.

While a specific embodiment of the present invention has been shown and described in detail to illustrate the application and principles of the invention, it will be understood that it is not intended that the present invention be limited hereto and that the invention may be embodied otherwise without departing from such principles.

What is claimed is:

1. A method for acoustically inspecting the coating integrity of the outer layer of a nuclear fuel particle comprising the steps of:

providing a database of load vs. acoustic emission signals for various nuclear fuel particles which were subjected to loads resulting in the cracking of the fuel particles;

determining from the provided database a threshold load level after which cracking of the fuel particles occurs;

subjecting a fuel particle to a controlled load up to the threshold load level;

measuring acoustic output signals during the period when the load exceeds the threshold load; and comparing the measured acoustic signals to provided database acoustic signals to determine the integrity of the fuel particle.

2. A method as set forth in claim 1 further comprising the step of subjecting a statistically determined number of fuel particles from a nuclear fuel particle bed to a controlled load to thereby determined the integrity of the bed.

3. A method as set forth in claim 1 wherein the step of measuring the acoustic output signals includes the step of measuring the acoustic signal duration from a first threshold crossing to a last threshold crossing.

4. A method as set forth in claim 3 further comprising the step of measuring a rise time from the first threshold crossing to a peak amplitude of the acoustic signal.

5. A method as set forth in claim 3 further comprising the step of measuring a peak amplitude of the acoustic signal duration.

* * * * *